United States Patent [19]
Dumbleton et al.

[11] Patent Number: 5,181,930
[45] Date of Patent: Jan. 26, 1993

[54] COMPOSITE ORTHOPEDIC IMPLANT

[75] Inventors: John H. Dumbleton, Ridgewood, N.J.; Ruey Y. Lin, New City, N.Y.; Casper F. Stark, Pompton Lakes, N.J.; Thomas E. Crippen, Ft. Worth, Tex.

[73] Assignee: Pfizer Hospital Products Group, Inc., New York, N.Y.

[21] Appl. No.: 683,391

[22] Filed: Apr. 10, 1991

[51] Int. Cl.⁵ .................. A61F 2/28; A61F 2/32; A61F 2/36
[52] U.S. Cl. ...................... 623/23; 623/16; 623/22
[58] Field of Search ............... 623/16, 22, 23, 18

[56] References Cited
U.S. PATENT DOCUMENTS

| | | | |
|---|---|---|---|
| 3,893,196 | 7/1975 | Hochman | 623/18 |
| 4,221,623 | 9/1980 | Heissler et al. | 156/169 |
| 4,329,743 | 5/1982 | Alexander et al. | 3/1 |
| 4,512,038 | 4/1985 | Alexander et al. | 3/1.9 |
| 4,662,887 | 5/1987 | Turner et al. | 623/16 |
| 4,714,467 | 12/1987 | Lechner et al. | 623/16 |
| 4,750,905 | 6/1988 | Koeneman et al. | 623/16 |
| 4,750,960 | 6/1988 | Bubeck | 156/169 |
| 4,778,469 | 10/1988 | Lin et al. | 623/16 |
| 4,892,552 | 1/1990 | Ainsworth et al. | 623/23 |
| 4,902,297 | 2/1990 | Devanathan | 623/16 |
| 4,978,360 | 12/1990 | Devanathan | 623/66 |

FOREIGN PATENT DOCUMENTS

| | | | |
|---|---|---|---|
| 0171884 | 2/1986 | European Pat. Off. | 623/16 |
| 0277727 | 3/1988 | European Pat. Off. | 623/22 |
| 9015708 | 12/1990 | World Int. Prop. O. | 623/16 |

OTHER PUBLICATIONS

"Stiffness and Strength tailoring of a hip prosthesis made of advanced composite materials", by Chang, F-K, Perez, J. L., and Davison, J. R., in Journal of Biomedical Materials Research, vol. 24, 1990, pp. 873-899.

Primary Examiner—David Isabella
Assistant Examiner—Dinh X. Nguyen
Attorney, Agent, or Firm—Peter C. Richardson; Lawrence C. Akers; Raymond W. Augustin

[57] ABSTRACT

A beam adapted for implantation within a bone is able to support bending and torsional loading forces applied thereto. The beam has a stiffness defined by a modulus elasticity, which stiffness varies along the length of the beam to match the corresponding stiffness of the cortical bone adjacent the beam after implantation within the bone. The beam is made from an elongated core formed of continuous filament carbon fibers embedded in a thermoplastic polymer matrix with the carbon filaments extending in a direction substantially parallel to the longitudinal axis of the beam. Encasing the core is a filler molded to the core, which filler is made up of the same thermoplastic polymer as the core but contains no reinforcing carbon fibers. The filler provides the prosthesis with a shape generally conforming to the desired shape of the final prosthetic implant. A sheath formed of carbon reinforced filament fibers embedded in the thermoplastic polymer is wound in spiral formation around the filler and molded thereto. The winding angle and the sheath thickness along the beam may be varied to vary the modulus of elasticity to match that of the cortical bone adjacent thereto.

20 Claims, 6 Drawing Sheets

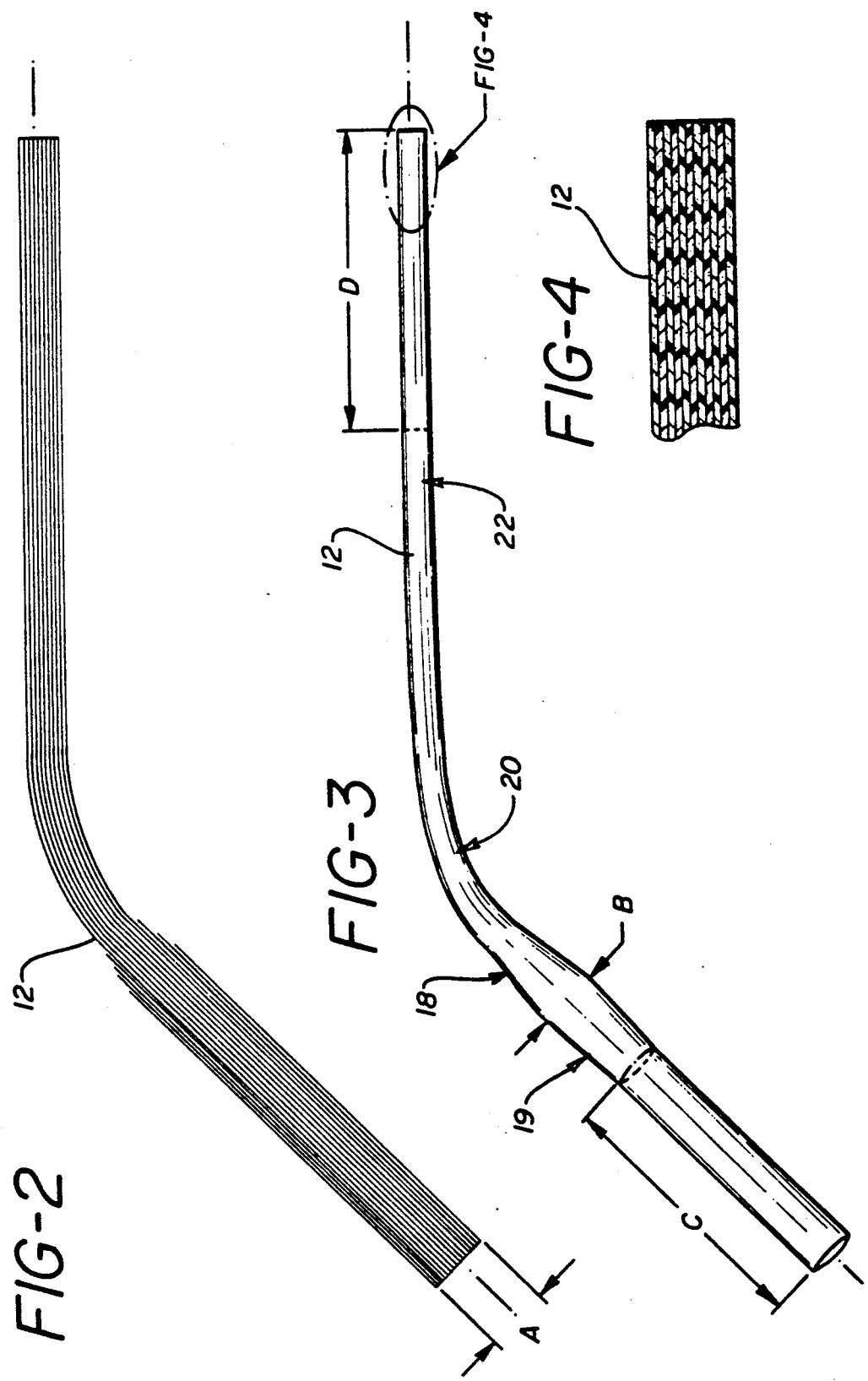

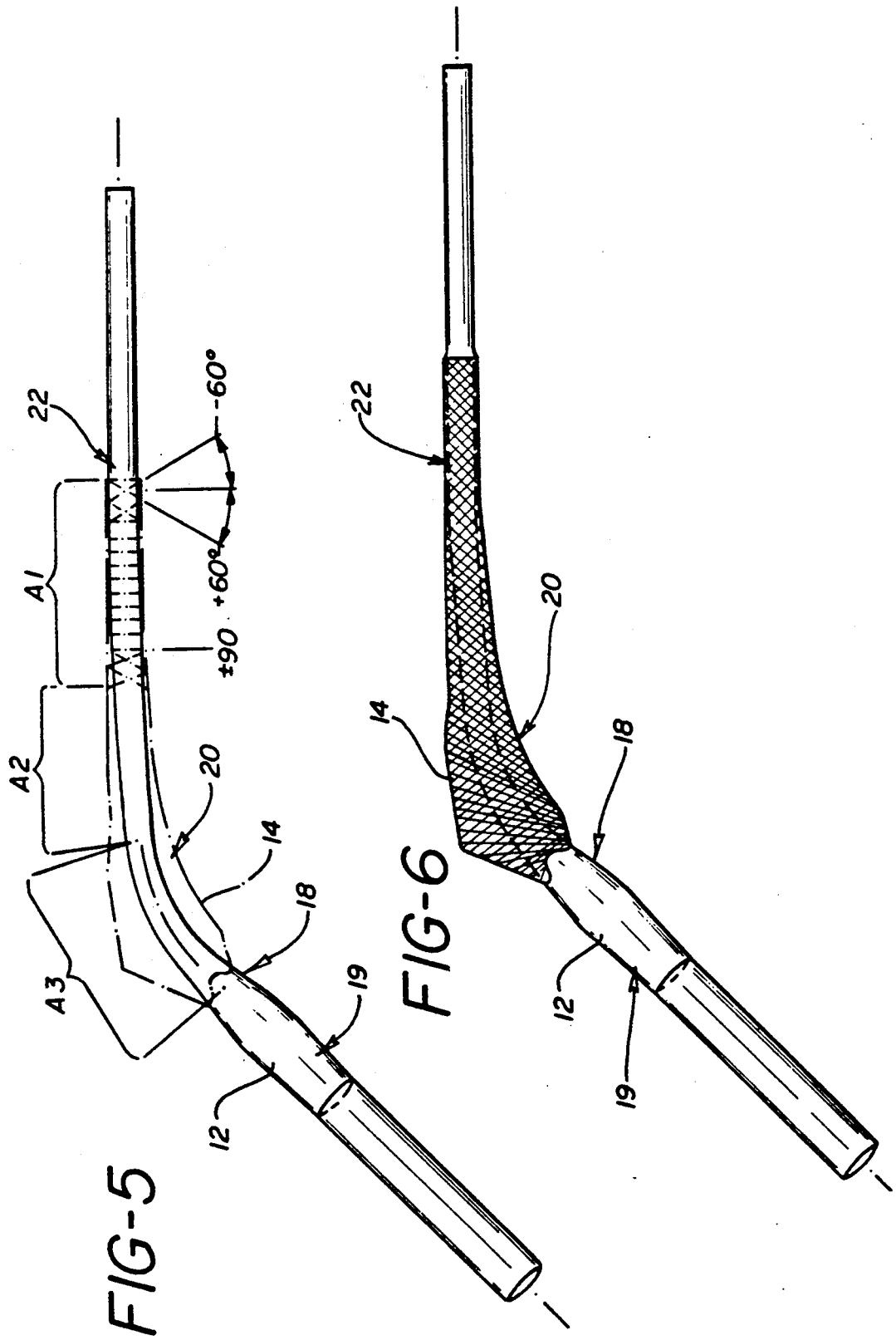

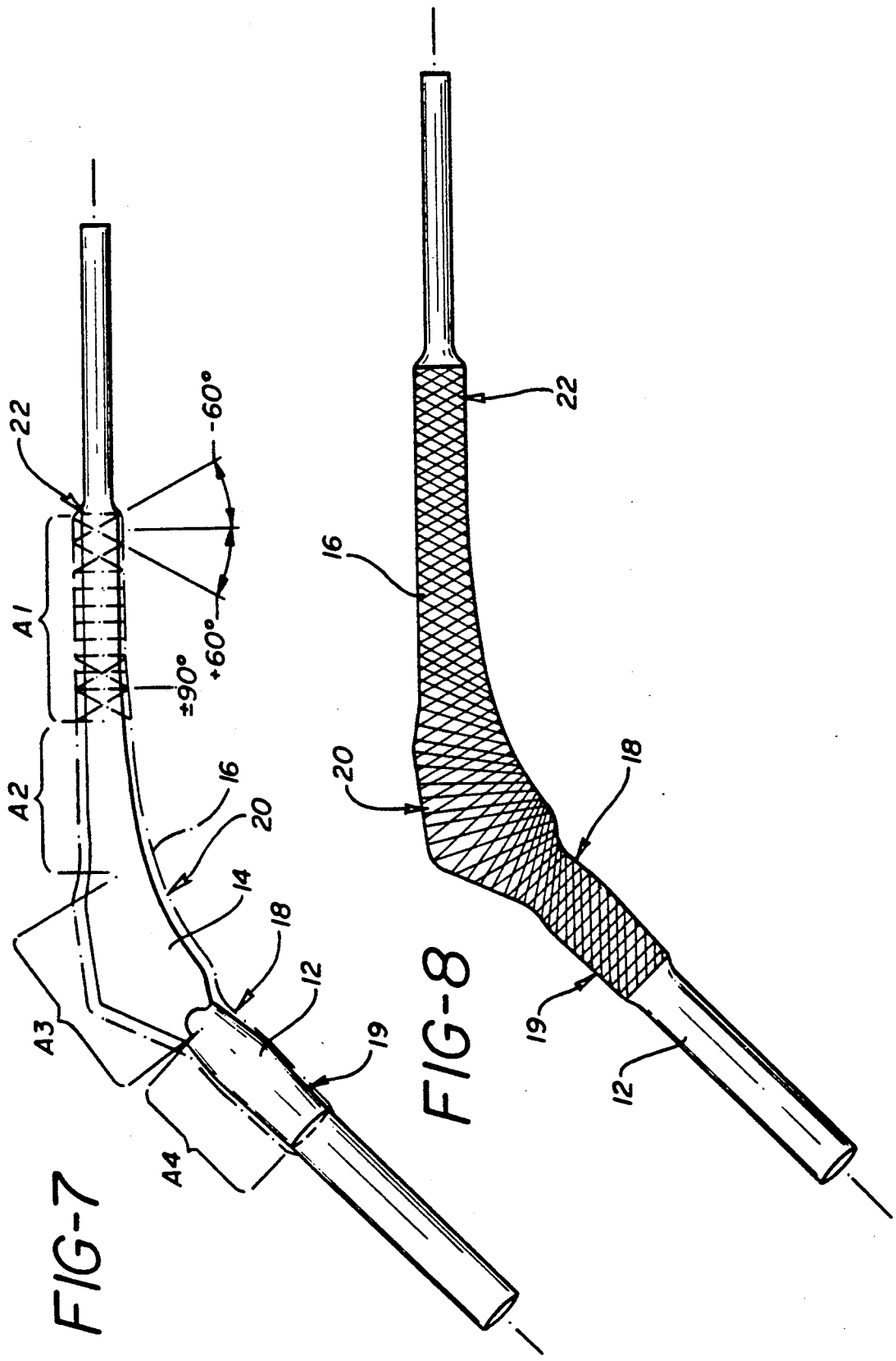

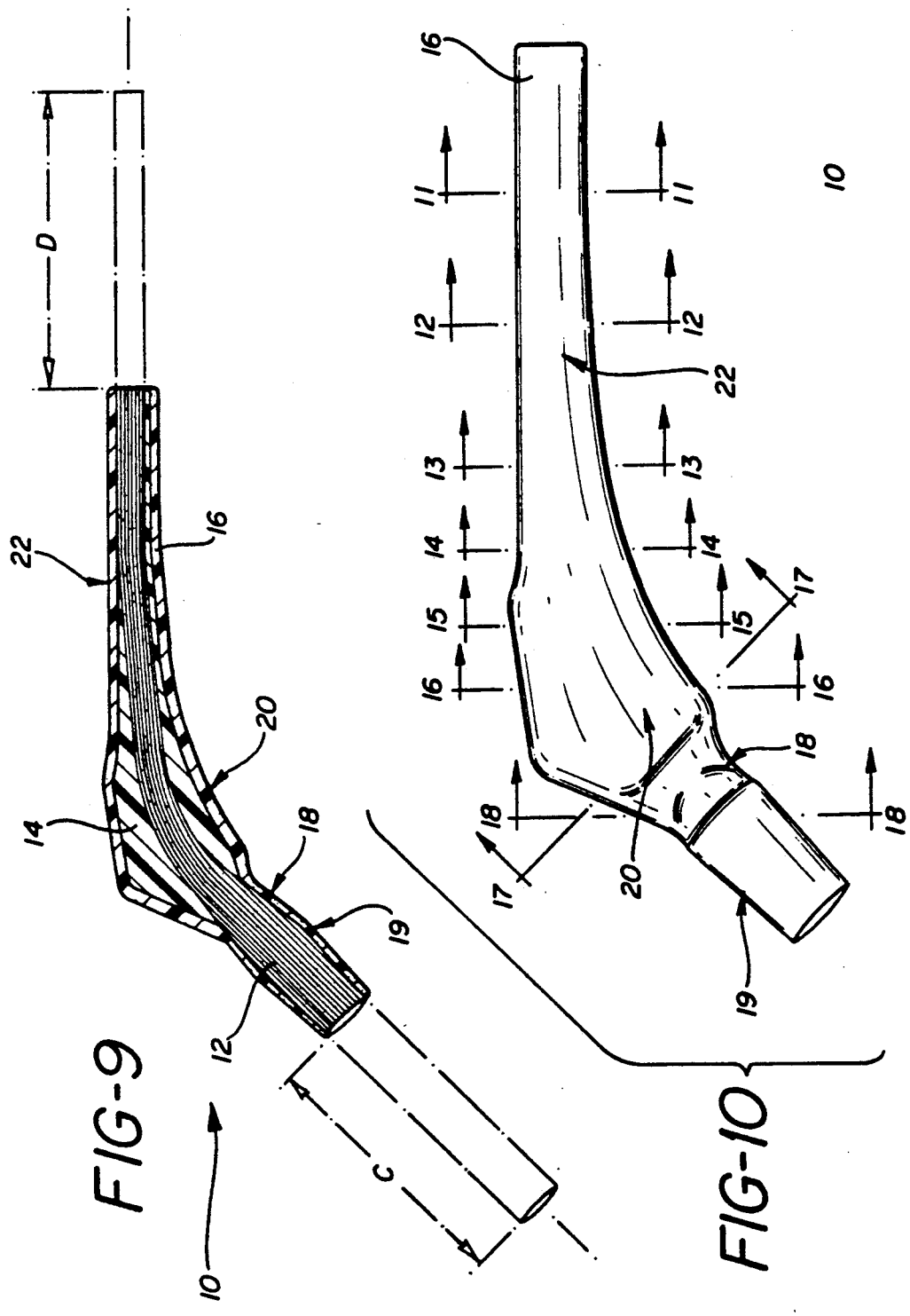

COMPOSITE ORTHOPEDIC IMPLANT

BACKGROUND OF THE INVENTION

1. Field of the Invention

The present invention relates to an improved composite stem construction and method, and particularly, to a composite stem construction for use in a load-bearing joint-replacement prosthetic device.

2. Description of the Prior Art

Stems for orthopedic implants which can withstand both bending and torsion loads are useful in a variety of orthopedic uses. One type of stem which has received considerable attention in the orthopedic field is for a hip joint replacement device. In basic design, this device includes an elongate curved stem which is adapted for receipt in a cavity formed in the proximal region of a femur, and a spherical head carried on a neck at the upper end of the stem. When implanted in operative position, the device functions as a load transfer member between the pelvis and femur, and as such, must accommodate considerable bending, axial compression and torsional forces applied across the joint to the femur.

Four basic constructions have been proposed previously for hip joint devices of this type. In three of these constructions, the curved stem is adapted for insertion into a bone cavity, and the neck is adapted to support the spherical head, usually via a conical trunion joint. Usually the stem and neck are formed as a single piece, and the spherical head is separately attached to the neck, preferably after inserting the stem into the bone. In one construction the stem and neck are formed as a unitary metal piece from stainless steel or, more preferably, from a cobalt chrome or titanium alloy. An advantage of an all metal construction is that the relatively thick metal stem and neck provide adequate bending and shear strength, so that problems of stem fracture or fatigue are minimal. A disadvantage of the construction is a high degree of stress on certain regions of the bone, and stress protection or shielding in other bone regions. Both high stress and stress shielding can cause bone deterioration and resorption, leading to areas of bone weakness and loss of bone support for the prosthesis.

The related problems of bone stress and stress protection which can occur in a hip joint replacement can be understood from the mechanics of weight load transfer across the hip joint device. Normally, much of the weight load is transferred to the femur near the upper joint region and this load is distributed to and carried by the underlying cortical bone region and the prosthesis stem. The distribution of forces in the underlying cortical region and prosthesis stem region is determined by the relative stiffness—or elastic modulus—of the bone and stem respectively. In normal bone, the elastic modulus of the outer cortical bone region is about $2.5 \times 10^6$ psi, and that of the softer interior cancellous region is less than $1 \times 10^6$ psi, so that weight loading forces are carried primarily by the outer cortical region. By contrast, the metal stem region of a prosthetic device, which replaces the soft cancellous region of bone, has an elastic modulus typically between about $15-35 \times 10^6$ psi, so that much more weight loading is carried by the stem, and much less by the outer cortical bone. In addition to the stress shielding this produces in the bone region adjacent the stem, the high-modulus stem also produces unnaturally high bone stress at the lower or distal tip of the stem, where forces carried in the stem are transmitted to the bone.

In a second known prosthesis construction, the stem and neck are formed from rolled or laminated layers of a composite material containing oriented carbon fibers embedded in a polymer resin. This construction is described generally in U.S. Pat. No. 4,892,552, which issued on Jan. 9, 1990, entitled "Orthopedic Device". In a preferred embodiment described therein, a series of composite layers containing fibers oriented in different directions are laminated, according to known composite block construction methods, to produce a machinable block whose different fiber orientations confer strength in different, selected directions with respect to the long axis of the block. The laminated block is then machined to produce a stem and neck piece which can be implanted in bone and fitted with a ball-like joint member. Since the laminate structure has a somewhat lower average elastic modulus, both in tension and shear, than a comparable size metal prosthesis, the above problems related to stress protection along the length of the prosthesis stem, and the high concentration of forces at the distal tip of the stem are somewhat reduced. However, the effective elastic moduli of the stem in tension and shear is still very high compared with the soft cancellous region of bone which the stem has replaced. Furthermore, the laminate material is generally not as strong as a comparable size metal stem, particularly at the neck region of the device where weight loading is borne entirely by the prosthesis. This is due in part to the fact that the carbon fibers oriented lengthwise in the stem do not follow the curvature of the stem, and generally do not extend along the entire length of the stem.

A third prosthesis construction which has been proposed in the prior art involves a metal core having a relatively large-diameter stem which is encased in a low-modulus polymer. A prosthesis of this type is described by Mathis, R., Jr., et al in "Biomechanics: Current Interdisciplinary Research" (Perren, M., et al, eds.) Martinus Nijhoff, Boston (1985) pp. 371-376. The combined modulus of the polymer and inner core of the device is much more like that of interior cancellous bone than is either a solid metal or laminate composite structure, and as a result, problems related to bone stress protection and high stress are reduced. This compound device has not been entirely satisfactory, however. One problem which has been encountered is fracturing at the neck/stem interface, due to large loading force applied at this juncture by the neck. A second problem is related to the cutting action of the relatively stiff metal core against the low-modulus polymer, in response to forces exerted on the stem in directions normal to the stem's long axis. Over an extended period, the cutting action can lead to core wobbling within the bone, and exaggerated movement of the core in response to loading.

In a fourth prior art device which is described in U.S. Pat. No. 4,750,905, which issued on Jun. 14, 1988, an elongate stem is designed to support a load capable of applying both bending and torsional load forces. The stem generally includes an elongate composite core formed of continuous-filament fibers oriented substantially along the length of the core and embedded in a polymer matrix. Where the core has a curved stem, such as in a hip joint replacement device, the fibers extend in a substantially uniform-density, non-distorted configuration from one end of the core to the other. The core is characterized by high tensile strength and elastic modulus, but relatively low shear strength and modulus.

The core is encased in a sheath which encases the stem and tapered section of the core, but not its upper neck. The sheath is made of braided or woven filaments which encircle the stem in a helical pattern extending along the encased portion of the core. The sheath filaments are bonded to the core by a thermoplastic polymer which is infused into the sheath and heat fused to the core. The polymer which embeds and bonds the sheath to the core is part of a thick polymer skin which forms the shape of the implant which fills the space of a bone cavity in which the device is received.

The problem with this device is that the bending modulus along the stem is fairly constant which can lead to higher than desirable stresses in some localized areas. There has been a need to find a simple way to make the stem stiffer in some areas and more flexible in others.

The implant of the present invention solves this problem by providing a stem with a different elastic modulus at different points along the length of the stem. This is done by placing a reinforcing outer wrap at the surface of the implant and varying the orientation of the reinforcing fibers of the outer wrap along the stem length.

In a circular structural member, it is the outer fibers which are most effective in providing resistance to bending and torsion, and which carry the major portion of the stress in doing so. The role of the outer wrap is to provide the hip prosthesis with the major resistance to bending and torsion required to achieve a design having the desired transfer index and design factor as defined hereinafter. The required contribution of the outer wrap to the desired rigidity and strength in each region of the prosthesis is accomplished by varying the orientation of the fibers in the wrap or the thickness of the wrap or both in that region. The outer wrap continues proximally out into the neck region so that joint loads applied to the neck can be transferred rapidly and smoothly to the outer wrap of the prosthesis body without having to be transmitted through the core of the stem below the neck. This is especially important when the outer wrap contacts cortical bone.

The core region of the stem of the present invention consists of unidirectional fibers in a matrix, aligned along the longitudinal axis of the core. The primary function of the core is to provide a strong, stiff neck. The core extends well within the body of the prosthesis in order to securely anchor the neck. The core is used also, although to a lesser degree than the outer wrap, to adjust the rigidity and strength of the body of the prosthesis to achieve the desired stem flexibility.

A filler region is located between the core and the outer wrap and is composed of a material having reduced structural rigidity. This region can act as a mandrel for fabricating the outer wrap. Because the filler contributes little to the overall rigidity of the prosthesis, it permits greater flexibility in adjusting the thickness (number of layers) of the outer wrap to achieve a desired rigidity and strength while maintaining a desired shape. The filler also helps define the shape of the prosthesis for proper fit and transfers stress from the core region to the outer wrap region.

SUMMARY OF THE INVENTION

It is an object of the invention to provide a beam for utilization in an orthopedic implant which has a varying modulus of elasticity along the length thereof which approximates that of the cortical bone adjacent the beam after implantation within a medullary canal. It is yet another object of the invention to provide a beam which is simple and economical to manufacture and which has properties which can be varied to meet a wide range of applications.

These and other objects of the invention are achieved by a beam adapted for implantation within a bone which is capable of supporting loads applied thereto in bending and torsion. The beam includes an elongated core formed of continuous filament fibers embedded in a thermoplastic polymer. These fibers are oriented substantially parallel to the longitudinal axis of the beam. Encasing the core is a filler composed of a non-reinforced thermoplastic polymer which is molded around the core to proximate the final desired shape of the prosthesis. A sheath is formed around the filler and is composed of carbon reinforced fibers embedded in a thermoplastic matrix, which is then spiral wound around the filler and molded thereto. The thermoplastic resin to make the core filler and sheath is polyetheretherketone. The sheath filament fibers are wound around the filler at angles with respect to the longitudinal axis of the core which vary along the axis of the core to produce a modulus of elasticity of the beam which varies along the length thereof.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

In the drawings wherein similar reference characters denote similar elements throughout the several views:

FIG. 2 is a side view of the hip prosthesis core prior to molding;

FIG. 3 is a side view of the core of FIG. 2 after molding;

FIG. 4 is an enlarged cross-sectional view of the distal stem shown in FIG. 3 showing the parallel alignment of the reinforcement fibers;

FIG. 5 is a view of a core of FIG. 3 showing the filler area in phantom, partially covered in the distal area by the first sheath layers;

FIG. 6 is a view of the core/filler of FIG. 5 having a first series of layers of sheath wound thereon;

FIG. 7 is a view of the core/filler of FIG. 6 with the final wound sheath outer dimension shown in phantom;

FIG. 8 is a view of the core/filler of FIG. 7 with the outer sheath completely wound thereon;

FIG. 9 is a cross-sectional view of the final composite prosthesis with the excess core shown in phantom;

FIG. 10 is a top view of the prosthesis of FIG. 9 after final molding; and

DETAILED DESCRIPTION OF THE INVENTION

Figure 1:
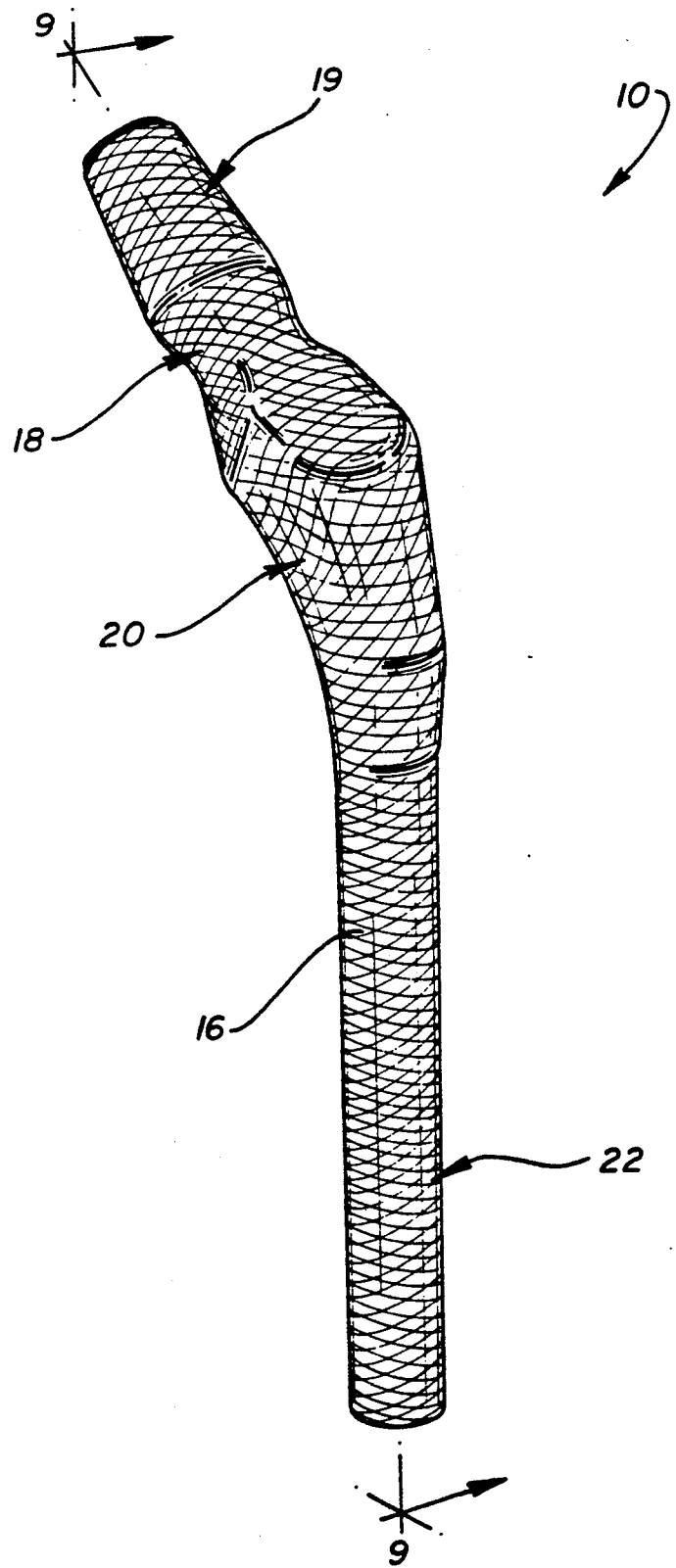
FIG. 1 is an isometric view of a hip prosthesis made in accordance with the present invention.
Figure 11:
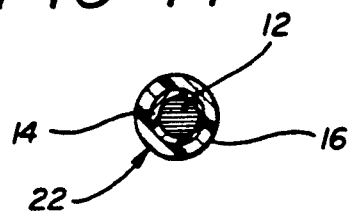
FIGS. 11–18 are cross-sectional views of the prosthesis of FIG. 10 along lines 11—11 through 18—18 respectively.
Figure 12:
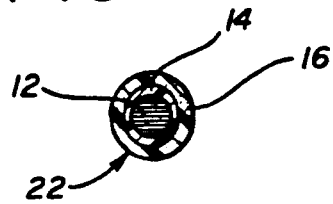
Figure 13:
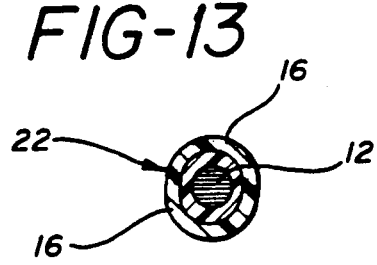
Figure 14:
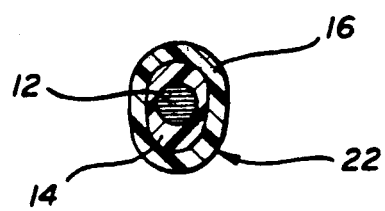
Figure 15:
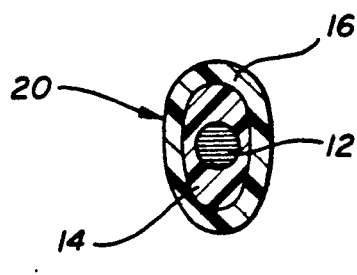
Figure 16:
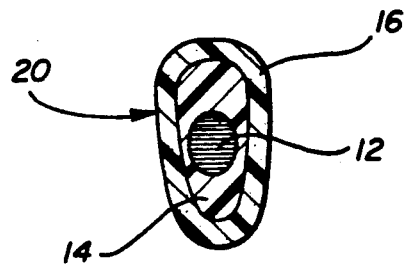
Figure 17:
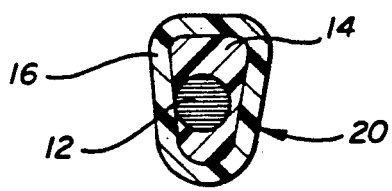
Figure 18:
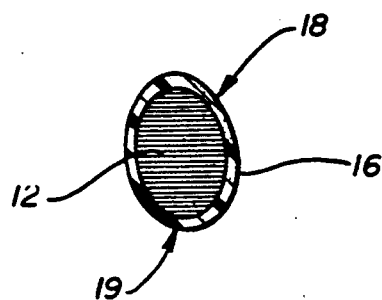

Referring first to FIG. 9, there is shown, in cross-section, the prosthesis of the present invention generally denoted as 10. Prosthesis 10 includes a core 12, a filler 14 and an outer wrap or sheath 16. The prosthesis 10, as shown, is a hip prosthesis, having a neck area 18, a proximal area 20 and a distal stem area 22. Neck area 18 includes a trunion 19 adapted to receive a spherical head (not shown).

In the preferred embodiment, core 12 extends the entire length of the prosthesis and, in order to provide for holding the prosthesis in a mandrel, may extend a predetermined distance beyond the ends of the desired final length of the prosthetic device. While in the preferred embodiment core 12 extends the entire length of the prosthetic device, it will be seen that the core is only structurally important in the neck area and that once the loading is transferred to the outer sheath 16 in neck area 18 of the prosthesis, the core serves no further structural function.

Referring to FIGS. 2-4, the core is shown to be made up of sheets of preimpregnated carbon fiber reinforced thermoplastic (prepreg) such as a polyetheretherketone (PEEK). The core is molded to the shape shown in FIG. 3 which, as stated above, includes sections C and D which extend beyond the desired length of the prosthetic core and are included merely for supporting the core in a mandrel for subsequent processing. FIG. 4 shows an enlarged view of the cross-section of the core containing 20-40 parallel sheets of prepreg thermoplastic, each about 0.005" thick, fused together.

Referring to FIGS. 5-8, there is shown the core 12 including a filler 14 molded therearound. Filler 14 is included to provide bulk material to help achieve the final desired shape of the prosthesis and to transfer stresses to the outer wrap. The filler/core is then wound with a sheath of either carbon fiber reinforced preimpregnated monofilament or preimpregnated carbon fiber reinforced sheets of narrow width such as ⅛". This material is wound at angles with respect to the core longitudinal axis, depending on the desired structural modulus along the various sections A1, A2, A3 of the stem. The orientation angles may be varied to match the modulus or elasticity of the prosthesis to the precalculated modulus of, for example, the human femur along the length of the beam or stem. The modulus of the cortical bone adjacent the femur medullary canal varies along the length of the femur and the sheath modulus may be varied to match this modulus.

Referring to FIG. 8 there is shown the final shape of the prosthesis after the core/filler combination has been wound with, in the preferred embodiment, a sheath or outer wrap containing 20-40 layers of reinforced thermoplastic (prepeg).

Referring to FIGS. 10-18 there is shown prosthesis 10 in its final molded condition with various cross-sections taken therethrough showing the outer sheath, inner core 12 with the filler 14 disposed therebetween.

As stated above, the figures disclose a stem 10 in the form of a beam for a prosthesis such as a hip prosthesis, designed in a manner to better match the stiffness of the hip stem to the human femur or any other bone. This design is done by computer modeling the composite structure. The model uses a Transfer Index (TI) as a measure of how effectively the load is transferred in a physiological manner from prosthesis to bone wherein:

$$TI = \frac{\text{Cortical Bone Stress with Implant}}{\text{Cortical Bone Stress Intact Bone}}$$

A TI value of 1.0 indicates perfect transfer, no change from the physiological case. Deviation from 1 indicates a mismatch in load transfer.

The analysis also uses a Design Factor (DF) as a measure of how close the computed stress in the prosthesis is to its limiting value.

$$DF = \frac{\text{Strength of Implant}}{\text{Stress Induced in Implant}}$$

The design factor should be greater than 1.0.

In the preferred embodiment the stem or beam structure consists of core 12, filler 14 and outer wrap 16 constructed to combine the necessary strength in the neck region, the required bulk to fill the bone cavity, and an outer wrap or sheath configured to reduce the stress gradient between bone and prosthesis while retaining strength.

This composite stem design dissipates loads quickly into bone in the proximal region 20, simulating the normal intact bone situation. Also the design permits the composite stem structure to be tailored to a specific bone geometry. Usually this is accomplished by using an anatomical data base for determining the desired size and shape. That is, filler region 14 can be changed to achieve adequate stem bulk and the outer sheath 16 wrap angles or thickness can be altered to maintain desired rigidity and strength along the length of the stem. In the preferred embodiment sheath 16 varies in thickness along the core/filler from about 0.07" in the distal stem area 22 to about 0.125" in the proximal/neck region. The thickness may be varied by varying the start and stop points of the wrapping at desired points along the stem or beam.

Using a simplified beam model of bone and prosthesis, the initial requirements for prostheses rigidity and strength are established using two load cases. These load cases involve the maximum load seen in the walking cycle and in rising from a chair. The model is then used to evaluate the many possible combinations of sheath fiber wrap orientation and sheath thickness until the desired properties are obtained. By observing transfer index patterns along the long axis of the stem, regions where rigidity changes are required can be identified. Rigidity is adjusted to a transfer index near 1.0, by changing outer sheath wrap or thickness design and to a lesser extent, the core, while maintaining sufficient strength (design factor).

Once the outer sheath, core and filler designs have been established by the simplified beam model, these designs are transferred to the commercially available ANSYS Finite Element Model consisting of 6092 nodes and 5472 elements. Analyses of material/bone configurations combining cortical and cancellous bone and prostheses leads to an evaluation of stem transfer index and design factor along the length of the beam or stem. Minor adjustments in wrap thickness or wrap angle of the outer sheath can be made as required.

It has been found from analyzing femurs that desired regional properties for a prosthetic hip stem are:

| Region | Modulus, psi |
| --- | --- |
| Stem Neck Region | $8.2 \times 10^6 \pm 10\%$ |
| Proximal Stem | $1.6 \times 10^6 \pm 10\%$ |
| Distal Stem | $1.1 \times 10^6 \pm 10\%$ |

In the preferred embodiment, stem modulus values are achieved by using the following carbon fiber reinforced PEEK sheath layers/outer wrap angles (with 0° being the longitudinal axial direction of the stem), of about 16 layers alternating at ±45° in the trunion/neck region (areas A3 and A4 of FIG. 7) In the proximal stem area (A3 of FIG. 7), two layers at +30° alternate with two layers at −30°, covered by eight at 90°, covered by two layers at −30° alternately with two at +30° for a total of 16 layers. In the distal stem area (A1 of FIG. 7) two layers at +60° alternate with two at −60°, covered by eight layers at 90°, then two at −60° alternating with two at +60°. These layers are placed over the unidirectional core in the neck area 18 and, in the case of the proximal and distal regions of the stem, filler 14. Each layer is about 0.005" thick.

This preferred construction of the stem is such that the outer sheath carbon fibers provide resistance to bending and torsion and carry the major portion of the stress while retaining the desired transfer index. By varying the orientation of the fibers of the outer wrap or thickness in a particular region of the beam or stem, the required contribution to rigidity and strength is achieved. The outer wrap continues proximally out into the neck to enable a smooth transference of joint load applied to the neck to the outer wrap of the stem body without transmission to the filler.

Table I shows examples of the effect of wrap angle on configuration on local composite stem properties. Note, however, that the total stem modulus is calculated from core, filler and sheath moduli at any point on the beam or stem.

TABLE I

| Outer Sheath Configuration | Modulus $\times 10^6$ psi | Fatigue Strength, Ksi |
| --- | --- | --- |
| $[0]_n$ (all n layers axial) | 19.1 | 145.0 |
| $[\pm 30°_2/90°_4]_s$* | 6.2 | 30.0 |
| $[\pm 40°_2/90°_4]_s$* | 4.1 | 20.1 |
| $[\pm 50°_2/90°_4]_s$* | 2.7 | 12.9 |
| $[\pm 60°_2/90°_4]_s$* | 1.9 | 9.1 |
| $[\pm 45°]_{4s}$* | 2.2 | 20.0 |
| $[90°]_{8s}$* | 1.3 | — |
| Filler (30% chopped carbon fiber) | 1.8 | — |
| Filler Only | 0.5 | — |

*±Θ$_2$ means four layers, two at +Θ alternating with two at −Θ. 90°$_4$ means four layers perpendicular to the longitudinal axis at a given point on the stem. The "s" refers to a mirror image repeat for a total of 16 layers.

0° indicates the longitudinal axis of the preferred core region 12 which consists of unidirectional carbon fibers in a thermoplastic matrix (prepreg) which fibers are aligned parallel to the longitudinal axis of the core. The primary function of core 12 is to provide a strong, stiff neck 18. Core 12 extends into the body of the stem to firmly anchor neck 18. Core 12 can also, to a lesser degree, influence the rigidity and strength of the body of the stem to achieve the desired transfer index and design factor. In the preferred embodiment the core varies in diameter from about 0.5" in the neck area 18 to about 0.25" in the distal stem area 22.

Filler 14 is composed of a reduced structural rigidity material, such as in the preferred embodiment non-reinforced thermoplastic material such as polyetheretherketone, contributing little to the overall rigidity of the prosthesis. Its basic use is for a mandrel for fabricating the outer wrap and to permit greater flexibility in overall thickness and shape of the implant. It also helps transfer stress from the core to the sheath. In the preferred embodiment the filler/core outer diameter is about 0.8" in the neck area and about 0.33" in the distal stem area. This dimension can be varied to match any desired final outer dimension for the prosthesis.

In the preferred method of manufacture core 12 is molded from sheets of prepreg reinforced with unidirectional carbon fiber. As shown in FIG. 1, a lay-up of these sheets cut to the approximate diameter of the final core are placed in a mold (not shown). As stated above, the carbon reinforcement fibers are all oriented in the direction of the longitudinal axis of the prosthesis. The mold is heated and then compressed to produce the core blank of FIG. 3. The core blank is the actual core of the prosthesis but extended in length at both ends to provide for later support in processing machines. The molding process forms the approximately 45° medial lateral (M-L) bend in the case of a hip stem so that the longitudinal axis of the stem is curved in the M-L plane.

After core 12 is molded it is then placed in an injection mold to produce the desired shape of filler 14. The mold is sized to produce the desired outer shape of the core plus filler. Molten polyetheretherketone is then injected into the mold and allowed to solidify. This process is well known in the art and is used extensively to produce plastic parts.

The filler may also be made from short or chopped fiber reinforced PEEK or from carbon fiber reinforced material wrapped at 90° around the core. In either case a modulus lower than about $2.0 \times 10^6$ is achieved.

As shown in FIGS. 5–8, after solidification the core/filler composite is then covered with a sheath of carbon fiber reinforced preimpregnated filament as discussed above. This may be accomplished either by wrapping the core/filler with carbon PEEK comingled yarn to form a series of layers or by wrapping with a thin (approximately ⅛" wide) strip or sheet of carbon fiber reinforced preimpregnated tape. Such a material may be in the form of preimpregnated ribbon or filament wound on a spool. The filament or tape is wound along the length of the core/filler to form layers at the predetermined angular orientations which may vary from layer to layer and/or within each layer. For example, a single sheath layer is a layer having fibers oriented at 60° to the longitudinal axis in the distal stem area 22, 45° in the proximal stem area 20 and 90° in the neck area 18 with transition areas at varying angles between the distal stem, proximal stem and neck areas. It should be noted that several layers contain wraps perpendicular to the central longitudinal axis ($\theta = 90°$) wound around the prosthesis core/filler. Since, for a hip prosthesis, the longitudinal axis includes a 35–55° bend in the plane parallel to the medial-lateral plane of the body, the filament fibers in these layers are not parallel to one another even though they are all perpendicular to the axis of the core/filler.

A strip/filament winding machine suitable for varying the angle of the filament with respect to the longitudinal axis of the core filler within a single layer or pass is disclosed in U.S. Pat. No. 4,750,960, the teachings of which are incorporated herein. Such a machine may be obtained from Automated Dynamics Corporation (ADC) in Schenectedy, N.Y. The machine winds the core filler with any number of layers of mono-filament or tape with the reinforcing fibers oriented in any desired pattern such as that described herein above.

Once the core/filler has been covered with the predetermined number of layers of preimpregnated filament or tape, the composite is placed in a final mold which conforms to the desired final shape. The material is heated to a temperature sufficient to cause the thermoplastic in the outer sheath to soften and then the composite structure is allowed to consolidate under pressure. If desired, the mold may include a roughened surface to impart such a surface to the outer surface of the prosthesis, such as for fixation enhancement by tissue ingrowth. Alternatively the method taught in U.S. Pat. No. 4,778,469 owned by the assignee of the present invention may be used to form an attachment surface on the outside of the composite stem.

While several examples of the present invention have been described, it is obvious that many changes and modifications may be made thereunto, without departing from the spirit and scope of the invention.

We claim:

1. A beam adapted for implantation within a bone to support a load capable of applying bending and torsional loading forces, comprising:
   an elongated core formed of continuous filament fibers oriented substantially parallel to a longitudinal axis of the beam and embedded in a thermoplastic polymer;
   encasing the core, a filler comprising a thermoplastic polymer molded to said core; and
   a sheath formed of filament fibers embedded in a thermoplastic polymer wound around the filler in a helical fashion to form layers and molded thereto wherein the core, the filler and the sheath each have a predetermined stiffness as defined by a modulus of elasticity wherein the core has a higher modulus of elasticity than the sheath and the sheath has a higher modulus of elasticity than the filler.

2. The beam as set forth in claim 1 wherein the filament fibers in said core and said sheath are carbon fibers impregnated with a thermoplastic resin.

3. The beam as set forth in claim 2 wherein said filler is composed exclusively of said thermoplastic resin.

4. The beam as set forth in claim 2 wherein said filler is composed of chopped carbon fiber embedded in said thermoplastic resin.

5. The beam as set forth in claim 4 wherein said thermoplastic resin is polyetheretherketone.

6. The beam as set forth in claim 1 wherein said sheath filament fibers are wound around said filler at angles with respect to said longitudinal axis of said core which vary along said axis of said core to ensure adequate bending and torsional strength in regions of the beam subjected to high stress.

7. The beam as set forth in claim 6 wherein said sheath filament fibers are wound around said filler at angles with respect to said longitudinal axis of said core which vary along said axis of said core to produce a modulus of elasticity of the beam which varies along the length thereof.

8. The beam as set forth in claim 1 wherein the modulus of elasticity of the core is greater than $10 \times 10^6$ psi, the modulus of elasticity of the filler is less than $2.0 \times 10^6$ psi and the modulus of the sheath varies from $1.5-10 \times 10^6$ psi.

9. The beam as set forth in claim 1 wherein the sheath is comprised of a plurality of discrete layers of said fibers, each oriented at predetermined angles with respect to the longitudinal axis of the beam to produce a beam having a stiffness at any point therealong generally corresponding to the stiffness of the bone adjacent the beam after implantation of the beam.

10. The beam as set forth in claim 9 wherein the angular orientation of said wound fibers varies within each discrete layer.

11. A beam adapted for implantation within a femur, said beam in the form of an implant having a neck region, a proximal stem region and a distal stem region, comprising:
    a core formed of filament fibers embedded in a thermo-plastic polymer oriented substantially along a longitudinal axis of the beam and extending between the proximal stem region and the neck region;
    a filler region, said filler region comprising a thermoplastic polymer molded to said core, said filler having a shape generally conforming to an outer shape of said hip implant;
    a sheath formed of filament fibers embedded in a thermoplastic polymer wound around the filler in discrete layers and molded thereto wherein the core, the filler and the sheath each have a predetermined stiffness as defined by a modulus of elasticity wherein the core has a higher modulus of elasticity than the sheath and the sheath has a higher modulus of elasticity than said filler.

12. The beam as set forth in claim 11 wherein the sheath is comprised of a plurality of discrete layers of said fibers oriented at various angles with respect to the longitudinal axis of the beam to produce a beam having a stiffness at any point therealong, generally corresponding to the stiffness of the femur adjacent the beam after the implantation thereof.

13. The beam as set forth in claim 12 wherein said thermoplastic polymer is polyetheretherketone.

14. A composite prosthetic hip stem comprising:
    a core molded from carbon fibers embedded in polyetheretherketone, said carbon fibers extending generally parallel to a longitudinal axis of the hip stem;
    a trunion formed at a proximal end of said core;
    a filler molded to said core, said filler comprising polyetheretherketone, said filler having a shape generally conforming to the desired shape of the prosthetic hip stem;
    a sheath formed of carbon fibers embedded in polyetheretherketone wound around the filler to form discrete layers and molded thereto, said sheath comprising a plurality of said layers of said fibers, each containing carbon fibers oriented at predetermined angles with respect to the longitudinal axis of the beam to produce a beam having a stiffness at any point therealong generally corresponding to the stiffness of the bone adjacent the beam after implantation of the beam wherein the core, the filler and the sheath each have a predetermined stiffness as defined by a modulus of elasticity wherein the core has a higher modulus of elasticity than the sheath and the sheath has a higher modulus of elasticity than said filler.

15. The hip stem as set forth in claim 14 wherein the angular orientation of said wound fibers varies within each discrete layer.

16. The hip stem of claim 14 wherein the filler is composed exclusively of polyetheretherketone.

17. The hip stem as set forth in claim 14 wherein said sheath filament fibers are wound around said filler at angles with respect to said longitudinal axis of said core which vary along said axis of said core to ensure adequate bending and torsional strength in regions of the beam subjected to high stress.

18. The hip stem as set forth in claim 14 wherein the modulus of elasticity of the core is greater than $10 \times 10^6$ psi, the modulus of elasticity of the filler is less than $2.0 \times 10^6$ psi and the modulus of the sheath varies from $1.5-10 \times 10^6$ psi.

19. The beam set forth in claim 1 wherein said sheath has a first and second portion formed of continuous filament fiber wrapped helically around said filler, said filament fiber in said first portion comprising two layers covering said filler oriented with respect to said axis at approximately $+30°$, covered by, two filament fiber layers at approximately $-30°$ to said axis, covered by, eight layers wrapped approximately perpendicular to said axis, covered by, four layers, two at approximately $-30°$ alternating with two at approximately $+30°$ to said axis, and said filament fiber in said second portion covering said filler comprising four layers, two at approximately $+60°$ alternating with two at approximately $-60°$ to said axis, covered by, eight layers wrapped perpendicularly to said axis, covered by, four layers, two at approximately $-60°$ alternating with two at approximately $-60°$.

20. The beam set forth in claim 14 wherein said sheath has a proximal and distal portion formed of continuous filament fiber wrapped helically around said filler, said filament fiber in said proximal portion comprising two layers covering said filler oriented with respect to said axis at approximately $+30°$, covered by two filament fiber layers at approximately $-30°$ to said axis, covered by, eight layers wrapped approximately perpendicular to said axis, covered by, four layers, two at approximately $-30°$ alternating with two at approximately $+30°$ to said axis, and said filament fiber in said distal portion covering said filler comprising four layers, two at approximately $+60°$ alternating with two at approximately $-60°$ to said axis, covered by, eight layers wrapped perpendicularly to said axis, covered by, four layers, two at approximately $-60°$ alternating with two at approximately $-60°$.

* * * * *